US011579133B2

(12) United States Patent
Campbell et al.

(10) Patent No.: US 11,579,133 B2
(45) Date of Patent: Feb. 14, 2023

(54) FAST WATER ACTIVITY MEASUREMENT SYSTEM

(71) Applicant: METER GROUP, INC. USA, Pullman, WA (US)

(72) Inventors: Scott H. Campbell, Pullman, WA (US); Gaylon S. Campbell, Pullman, WA (US); Benjamin J. Walden, Moscow, ID (US); Zachary J. Campbell, Pullman, WA (US)

(73) Assignee: METER GROUP, INC. USA, Pullman, WA (US)

( * ) Notice: Subject to any disclaimer, the term of this patent is extended or adjusted under 35 U.S.C. 154(b) by 74 days.

(21) Appl. No.: 16/820,507

(22) Filed: Mar. 16, 2020

(65) Prior Publication Data

US 2021/0285925 A1    Sep. 16, 2021

(51) Int. Cl.
*G01N 33/10* (2006.01)
*G01K 7/02* (2021.01)
*G01N 27/22* (2006.01)

(52) U.S. Cl.
CPC ............... *G01N 33/10* (2013.01); *G01K 7/02* (2013.01); *G01N 27/223* (2013.01)

(58) Field of Classification Search
CPC .... G01N 27/223; G01N 31/10; G01N 33/246; G01K 7/02
See application file for complete search history.

(56) References Cited

U.S. PATENT DOCUMENTS

2007/0087101 A1 * 4/2007 Gusek ................... A21D 2/266
                                                        426/549
2012/0079876 A1    4/2012 Stroock et al.
(Continued)

FOREIGN PATENT DOCUMENTS

WO      2011079367 A1    7/2011
WO   WO-2014091372 A1 *  6/2014 ............. G01N 33/02
WO      2014201442 A1   12/2014

OTHER PUBLICATIONS

Aqualab Water Activity Meter Operators Manual for series 4. Mar. 29, 2019. https://www.metergroup.com/food/products/aqualab-4te-water-activity-meter/ Retrieved Oct. 13, 2021 (Year: 2019).*
(Continued)

*Primary Examiner* — Nimeshkumar D Patel
*Assistant Examiner* — Jean F Morello
(74) *Attorney, Agent, or Firm* — Dorsey & Whitney LLP

(57) ABSTRACT

Methods and system for determining water activity of a sample material are disclosed in which a sample material is positioned in a water activity measurement device, a plurality of water activity values of the sample material are measured at a respective plurality of points of time, with the plurality of points in time preceding an equilibrium state of the water activity of the sample material, the plurality of water activity values over time are log-transformed, a trendline of the plurality of water activity values over time is calculated, and the trendline is extrapolated to determine an extrapolated water activity value of the sample material at the equilibrium state. These methods and systems can decrease the time needed to determine the water activity of the sample by reliably predicting and estimating water activity well before equilibrium is reached in the measurement chamber.

23 Claims, 6 Drawing Sheets

(56) References Cited

U.S. PATENT DOCUMENTS

2013/0046483 A1 2/2013 Mansouri et al.
2017/0124463 A1 5/2017 Chen et al.

OTHER PUBLICATIONS

P R Armstrong et al. "Design and Testing of an Instrument to Measure Equilibrium Moisture Content of Grain") Applied Engineering in Agriculture, Jan. 1, 2009, pp. 617-624. retrieved https://elibrary.asabe.org Oct. 13, 2021 (Year: 2008).*
Extended European Search Report received for European Application No. 21160745.2, dated Jul. 19, 2021, 7 pages.
Water Activity Measurement—Moisture Meter—Measurement and Monitoring of AW Value, retrieved Sep. 22, 2022 from https://www.rotronic.com/en-us/humidity-measurement-feuchtemessung-temperaturmessungs/water-activity.
LabMaster-aw neo, retrieved Sep. 22, 2022 from https://www.novasina.ch/produkt/labmaster-aw-neo/, 8 pp.
Best Water Activity Meters 2019: The Definitive Guide, retrieved Sep. 22, 2022 from https://wateractivity.org/, 2019, 11 pp.

* cited by examiner

FAST WATER ACTIVITY MEASUREMENT SYSTEM

TECHNICAL FIELD

The present disclosure generally relates to instruments and methods used to measure water activity in a sample material and specifically relates to instruments and methods used to determine or predict the water activity value of a sample before it reaches an equilibrium state in a water activity testing device.

BACKGROUND

Water activity and water potential are measures of the energy state of water in hydrated systems such as foods and soils. Knowledge of the water activity of a system is desirable to understand how the system behaves. For example, water activity affects the availability of water for plant or microbial growth and water movement in a system is due to gradients in water activity or water potential. Water activity is one of the most important measurements there is for determining whether a food or pharmaceutical product will be safe, stable, and function properly. The measurement is needed in laboratories, but also on the production floor to determine whether a product has dried sufficiently or been hydrated to the proper level.

Water activity is conventionally measured by equilibrating the water in the sample with an external surrounding phase (i.e., gas, liquid or solid) and then measuring the water activity in the equilibrated phase. When a test sample is initially positioned in a chamber of a testing instrument, the sample and its immediate surroundings are not in equilibrium, and the user must wait to obtain the water activity reading, sometimes for extended periods of time, until equilibrium is reached. Additionally, in some cases, equilibrium is difficult or impossible to reach because the chamber itself takes up water, and sample materials and other impurities in the testing chamber can slow or prevent equilibration. There is therefore a constant need for improvements to water activity measurements and instrumentation.

SUMMARY

One aspect of the present disclosure relates to a method of determining water activity of a sample material by positioning a sample material in a water activity measurement device, measuring a plurality of water activity values of the sample material at a respective plurality of points of time, with the plurality of points in time preceding an equilibrium state of the water activity of the sample material, log-transforming the plurality of water activity values over time, calculating a trendline of the plurality of water activity values over time, and extrapolating the trendline to determine an extrapolated water activity value of the sample material at the equilibrium state.

In some embodiments, the extrapolated water activity value of the sample material at the equilibrium state can be determined before the sample material reaches the equilibrium state in the water activity measurement device. In some embodiments, the method can further comprise discarding a group of the plurality of water activity values corresponding to an initial portion of the plurality of points of time before calculating the trendline. Positioning the sample material can comprise enclosing the sample material in a sealed chamber of the water activity measurement device. The plurality of water activity values can all be determined within a measurement time duration of up to about 60 seconds, and the plurality of points in time can occur at about one second intervals.

In some embodiments, the method further comprises detecting a physical or chemical characteristic of the sample material and determining a predicted time at which the equilibrium state of the water activity of the sample material will be reached before calculating the trendline, wherein the extrapolated water activity value is extrapolated to occur at the predicted time.

In some embodiments, the method can further comprise comparing the extrapolated water activity value to a target threshold range having an error range, and if the extrapolated water activity value is within the error range: producing an indicator indicating that the extrapolated water activity value is within the error range, and if the extrapolated water activity value is outside the error range: producing an indicator of the water activity value indicating whether or not the extrapolated water activity value is within the target threshold range.

In yet another embodiment, the method can further comprise comparing the extrapolated water activity value to a target threshold range having an error range; and if the extrapolated water activity value is within the error range: measuring a second plurality of water activity values of the sample material at a respective second plurality of points of time, log-transforming the first and second plurality of water activity values over time, calculating a second trendline of the first and second pluralities of water activity values over time, and extrapolating the second trendline to determine a second extrapolated water activity value of the sample material at the equilibrium state.

Another aspect of the disclosure relates to a water activity measurement apparatus, comprising: a measurement chamber, a water activity sensor in the measurement chamber, a processor, memory in electronic communication with the processor, and instructions stored in the memory. The instructions can be executable by the processor to determine, by the water activity sensor, a plurality of water activity values of a sample material in the measurement chamber over a respective plurality of points in time, the plurality of points in time preceding an equilibrium state of the water activity of the sample material, log-transform the plurality of water activity values over time, calculate a trendline of the plurality of water activity values over time, and extrapolate the trendline to determine an extrapolated water activity value of the sample material at the equilibrium state.

In some embodiments, the instructions can be configured to determine the extrapolated water activity value of the sample material at the equilibrium state before the sample material reaches the equilibrium state in the water activity measurement device. The instructions can further comprise discarding a group of the plurality of water activity values corresponding to an initial portion of the plurality of points of time before calculating the trendline. The plurality of water activity values can be configured to all be determined within a measurement time duration of up to about 60 seconds.

In some embodiments, the apparatus has instructions that are further executable to detect a physical or chemical characteristic of the sample material and determine a predicted time at which the equilibrium state of the water activity of the sample material will be reached before calculating the trendline, wherein the extrapolated water activity value is extrapolated to occur at the predicted time.

In some embodiments, the instructions can be further executable to compare the extrapolated water activity value to a target threshold range having an error range, and if the extrapolated water activity value is within the error range: measure a second plurality of water activity values of the sample material at a respective second plurality of points of time, log-transform the first and second plurality of water activity values over time, calculate a second trendline of the first and second pluralities of water activity values over time, and extrapolate the second trendline to determine a second extrapolated water activity value of the sample material at the equilibrium state.

Yet another aspect of the disclosure relates to a non-transitory computer-readable medium storing computer-executable code for measuring water activity of a sample material, wherein the code is executable by a processor to: determine, by a water activity sensor, a plurality of water activity values of a sample material in a measurement chamber over a respective plurality of points in time (with the plurality of points in time preceding an equilibrium state of the water activity of the sample material), log-transform the plurality of water activity values over time, calculate a trendline of the plurality of water activity values over time, and extrapolate the trendline to determine an extrapolated water activity value of the sample material at the equilibrium state.

In some embodiments, the instructions can be configured to determine the extrapolated water activity value of the sample material at the equilibrium state before the sample material reaches the equilibrium state in the water activity measurement device. The instructions can also further comprise discarding a group of the plurality of water activity values corresponding to an initial portion of the plurality of points of time before calculating the trendline. The plurality of water activity values can be configured to all be determined within a measurement time duration of up to about 60 seconds.

In some embodiments, the instructions can be further executable to detect a physical or chemical characteristic of the sample material and determine a predicted time at which the equilibrium state of the water activity of the sample material will be reached before calculating the trendline, wherein the extrapolated water activity value is extrapolated to occur at the predicted time.

In some embodiments, the instructions can be further executable to compare the extrapolated water activity value to a target threshold range having an error range, and if the extrapolated water activity value is within the error range: measure a second plurality of water activity values of the sample material at a respective second plurality of points of time, log-transform the first and second plurality of water activity values over time, calculate a second trendline of the first and second pluralities of water activity values over time, and extrapolate the second trendline to determine a second extrapolated water activity value of the sample material at the equilibrium state.

The above summary is not intended to describe each embodiment or every implementation of the present disclosure. The Figures and the detailed description that follow more particularly exemplify one or more example embodiments.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

Figure 1:
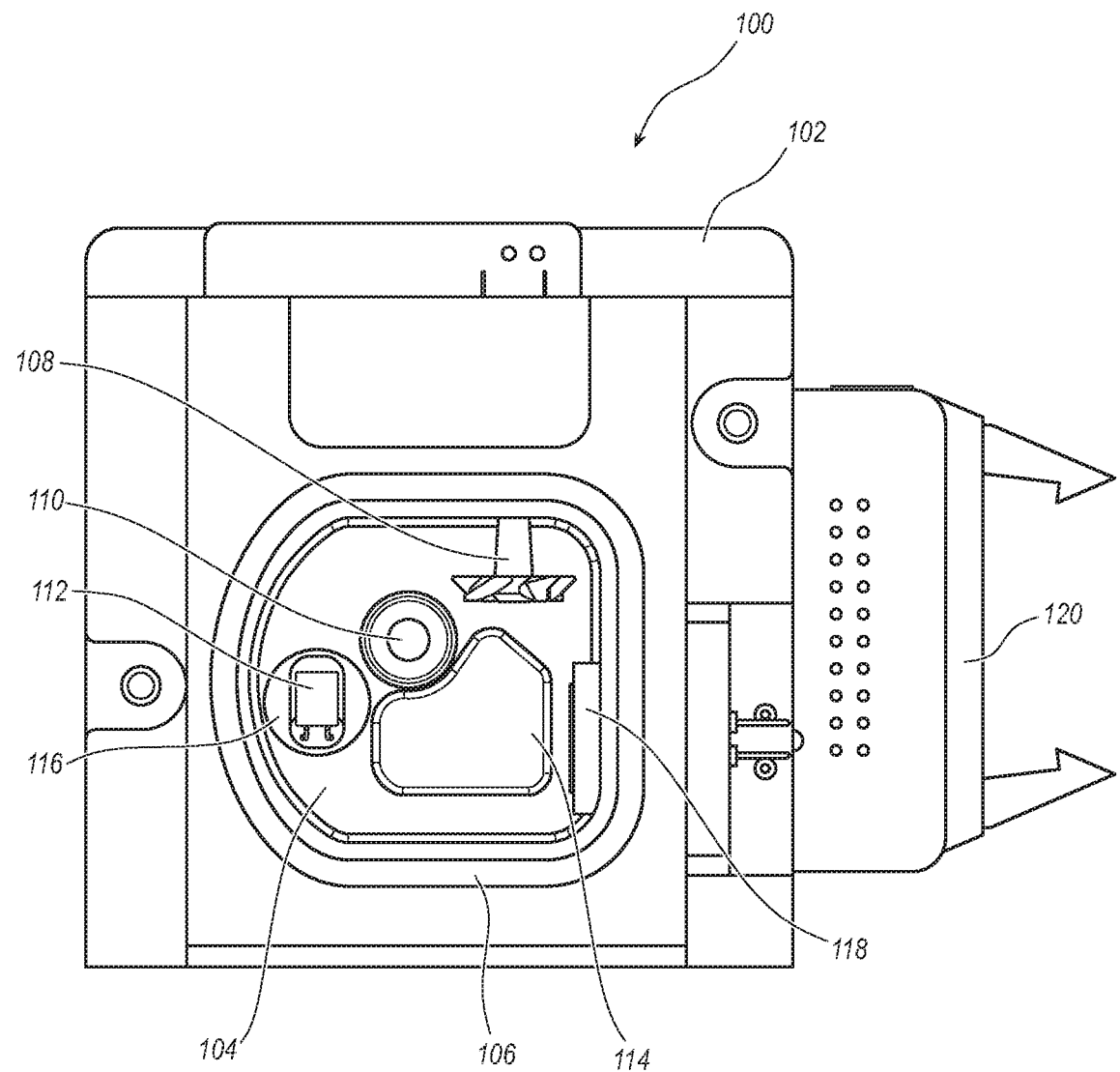
FIG. 1 is a diagrammatic bottom view of a water activity meter.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

Typical water activity measurements can take 5 to 30 minutes to perform and are therefore too slow for controlling manufacturing processes on a factory floor. If the water activity of the sample product is determined to be out of its acceptable range of values, a potentially large amount of unacceptable product is produced before the water-activity-related problem is detected. In other words, by the time a reliable water activity measurement is obtained for a sample of a product, 5 to 30 minutes worth of production of the product has passed. This can be an especially difficult issue to manage in facilities where ambient relative humidity or the water activity of products varies significantly based on the time of year, weather, the number of suppliers, and related factors.

Aspects of the present disclosure relate to obtaining accurate water activity measurements of sample materials within a very short period of time, including, for example, in about one minute or less. By obtaining water activity measurements in such a short period of time, measurements can be made on a factory floor and users can make quick adjustments to production processes to optimize water activity in the products before large amounts of the product have been produced and end up wasted or otherwise unacceptable. Thus, testing water activity can be simpler, faster, and easier to do.

In an example embodiment, a system of the present disclosure includes measuring water activity values of a sample material over time starting immediately after the sample material is inserted into a water activity measurement device. The water activity values are collected in high-resolution and at high frequency over time as compared to conventional measurement methods. In some cases, the readings can be gathered about once per second using a high-frequency sensor such as a capacitive relative humidity sensor. Readings can be simultaneously measured using a slower sensor, such as a chilled mirror dew point sensor, at a slower frequency and at the same time as the high-frequency sensor. Many types of common sample materials have water activity value measurements that decrease rapidly at first and then slowly decrease (i.e., with a declining rate of change) until a relatively constant and stable value is reached for the sample water activity due to the sample reaching equilibrium in the testing device. As explained above, reaching equilibrium can often take about 5 to 30 minutes. However, the initial rapid change in water activity value measurements, followed by the gradual decrease in the rate of change, causes the water activity values to follow a logarithmic curve when properly tracked and recorded. Thus, in embodiments of the present disclosure, the collected water activity values can be gathered in a short, preset length of time (e.g., for about 60 seconds) that is less than the time needed for the sample to reach equilibrium, and after the preset amount of time has elapsed, the collected water activity values can be log-transformed. The log-transformed values may have a substantially linear relationship to log-transformed time values. Thus, the first 60 seconds of water activity measurements can be collected and log-transformed into a generally straight line of values over time.

A trendline of the plurality of water activity values over time can then be calculated. For many types of materials, such as, for example, food products, this trendline can be a close approximation of the water activity values over time, even well past the first 60 seconds of measurements. Accordingly, the trendline can be used to extrapolate the water activity value of the sample material at a future time, such as when the sample material has reached an equilibrium state in the water activity measurement device, so the system can predict the water activity value without having to wait for several (e.g., four or more) minutes for that equilibrium state to be reached. These predicted water activity values can have high accuracy in a very short amount of time.

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

Turning now to the figures, FIG. 1 is a bottom end view of the water activity meter 100 suitable for use as part of a water activity measurement system according to the present disclosure. The water activity meter 100 can be referred to as a water activity measurement device or a water activity sensor. The water activity meter 100 can comprise a housing 102 having an internal chamber 104 in which a sample material (not shown) can be positioned for measurements and testing. The internal chamber 104 can be sealed against air or vapor intrusion while a sample is being tested. For example, the water activity meter 100 can have an o-ring 106 or similar seal around an access port through which the sample material is inserted into the internal chamber 104. In this manner, the internal chamber 104 can be a sealed system and substantially isolated from the surrounding environmental conditions. In some cases, the housing 102 can have a drawer, a door, a tray, a capsule, a similar tool or device, or combinations thereof for opening the internal chamber 104 and positioning a sample material within.

The internal chamber 104 can be filled with air while a sample material is being tested. A chamber fan 108 can be positioned within the internal chamber 104 and can be operated to circulate the air in the chamber 104 so that equilibrium in the chamber is reached more quickly and so that the air in the chamber 104 at any given time has substantially consistent properties throughout the chamber 104. The fan 108 can comprise fins, such as a propeller or impeller, to force circulation within the chamber 104.

A suite of sensors can be positioned within the internal chamber 104 for the monitoring and measurement of the sample material by the water activity meter 100. For example, as shown in FIG. 1, a temperature sensor 110 (e.g., a thermopile), a humidity sensor 112, and an optical sensor 114 can be configured to take readings and measurements of the air or of the sample material itself before, during, or after a test. In some embodiments, a filter 116 and a mirror 118 can be used to enhance the testing process and reduce error and uncertainty from the measurements obtained by the sensors 110, 112, 114. For instance, the filter 116 can remove contaminants or invasive unwanted materials from the air in the internal chamber 104 before or during testing. The mirror 118 is cooled electronically until dew is sensed on its surface by the optical sensor 114 to determine dew point temperature, from which water activity can be determined. The chamber 104 can be temperature-controlled to avoid condensation.

The housing 102 can also be connected to electronic components, such as computer components including a processor and a memory device in electronic communication with the electronic components of the internal chamber 104, such as the fan 108, the thermal sensor 110, the humidity sensor 112, the optical sensor 114, and, in some cases, the filter 116 and the mirror 118. See also FIG. 2. Accordingly, the electronic components of the housing 102 can be configured to receive electronic signals and measurements made by all of the instruments in the internal chamber 104 where testing takes place of a sample material. Furthermore, the electronic components of the housing 102 can be electronically connected to an external device, such as an external computing device (see devices 228 in connection with FIG. 2 below), by a wired or wireless electronic communications interface, such as, for example, a pin connector 120, an antenna, a user input device, a user output device, a data storage device (e.g., and electronic information storage device), similar devices, and combinations thereof.

Figure 2:
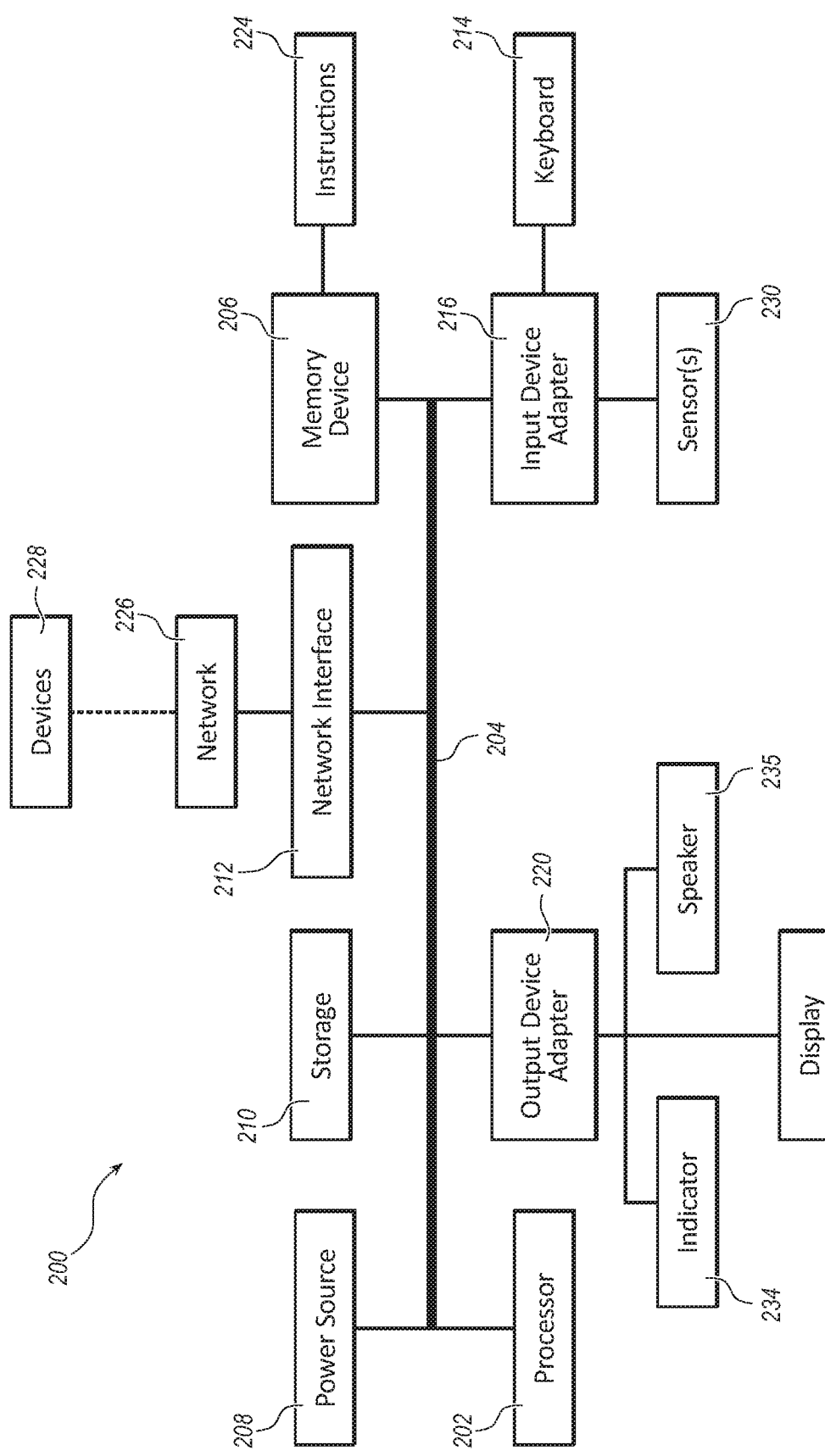
FIG. 2 is a block diagram of a computer system for measuring water activity.

FIG. 2 shows a high-level block diagram of a computer system 200 of embodiments of the present disclosure. In various embodiments, the computer system 200 can comprise various sets and subsets of the components shown in FIG. 2. Thus, FIG. 2 shows a variety of components that can be included in various combinations and subsets based on the operations and functions performed by the system 200 in different embodiments. It is noted that, in connection with this figure or others in this disclosure, when described or recited herein, the use of the articles such as "a" or "an" is not considered to be limiting to only one, but instead is intended to mean one or more unless otherwise specifically noted herein.

The computer system 200 can comprise a central processing unit (CPU) or processor 202 connected via a bus 204 for electrical communication to a memory device 206, a power source 208, an electronic storage device 210, a network interface 212, an input device adapter 216, and an output device adapter 220. For example, one or more of these components can be connected to each other via a substrate (e.g., a printed circuit board or other substrate) supporting the bus 204 and other electrical connectors providing electrical communication between the components. The bus 204 can comprise a communication mechanism for communicating information and signals between parts of the system 200.

The processor 202 can be a microprocessor or similar device configured to receive and execute a set of instructions 224 stored by the memory 206. The memory 206 can be referred to as main memory, such as random access memory (RAM) or another dynamic electronic storage device for storing information and instructions to be executed by the processor 202. The memory 206 can also be used for storing temporary variables or other intermediate information during execution of instructions executed by the processor 202. The storage device 210 can comprise read-only memory (ROM) or another type of static storage device coupled to the bus 204 for storing static or long-term (i.e., non-dynamic) information and instructions for the processor 202. For example, the storage device 210 can comprise a magnetic or optical disk (e.g., hard disk drive (HDD)), solid state memory (e.g., a solid state disk (SSD)), or a comparable device. The power source 208 can comprise a power supply capable of providing power to the processor 202 and other components connected to the bus 204, such as a connection to an electrical utility grid or a battery system.

The instructions 224 can comprise information for executing processes and methods using components of the system 200. Such processes and methods can include, for example, methods described in connection with FIGS. 3-6 and elsewhere herein.

The network interface 212 can comprise an adapter for connecting the system 200 to an external device via a wired or wireless connection. For example, the network interface 212 can provide a connection to a computer network 226 such as a cellular network, the Internet, a local area network (LAN), a separate device capable of wireless communication with the network interface 212, other external devices or network locations, and combinations thereof. In one example embodiment, the network interface 212 is a wireless networking adapter configured to connect via WI-FI®, BLUETOOTH®, BLE, a cellular or mobile digital modem or interface, a Bluetooth mesh, or a related wireless communications protocol to another device having interface capability using the same protocol. In some embodiments, a network device or set of network devices 228 in the network 226 can be considered part of the system 200. For example, in some cases, one or more network devices 228 can be connected to, but not a part of, the system 200.

The input device adapter 216 can be configured to provide the system 200 with connectivity to various input devices such as, for example, a keyboard 214, one or more sensors 230 (e.g., the sensors from FIG. 1), related devices, and combinations thereof. In an example embodiment, the input device adapter 216 is connected to a set of sensors including a thermometer or thermopile, a capacitive relative humidity sensor, an image sensor, a laser, a force sensor, and other sensors for detecting water activity or other properties of a sample material. In some embodiments, a subset of, or additional, sensor devices can be used. Thus, the sensors 230 can be used to transduce various properties of sample products and their surroundings in the water activity measurement device. The keyboard 214 or another input device (e.g., buttons or switches) can be used to provide user input such as input regarding the settings of the system 200. In some embodiments, information about a sample material, such as its expected time to equilibriation, can be input or provided using input devices (e.g., 214) or can be provided electronically from another device 228 on the network 226, such as an external server or other network-attached computing device having sample material data stored thereon. Thus, in some cases, a remote data repository can be accessible by the system 200 to obtain information about a sample material, such as its typical equilibriation time for a water activity measurement.

The output device adapter 220 can be configured to provide the system 200 with the ability to output information to a user, such as by providing visual output using one or more displays 232 or other indicators 234, such as by providing audible output using one or more speakers 235. Other output devices can also be used. The processor 202 can be configured to control the output device adapter 220 to provide information to a user via the output devices connected to the adapter 220.

Figure 3:
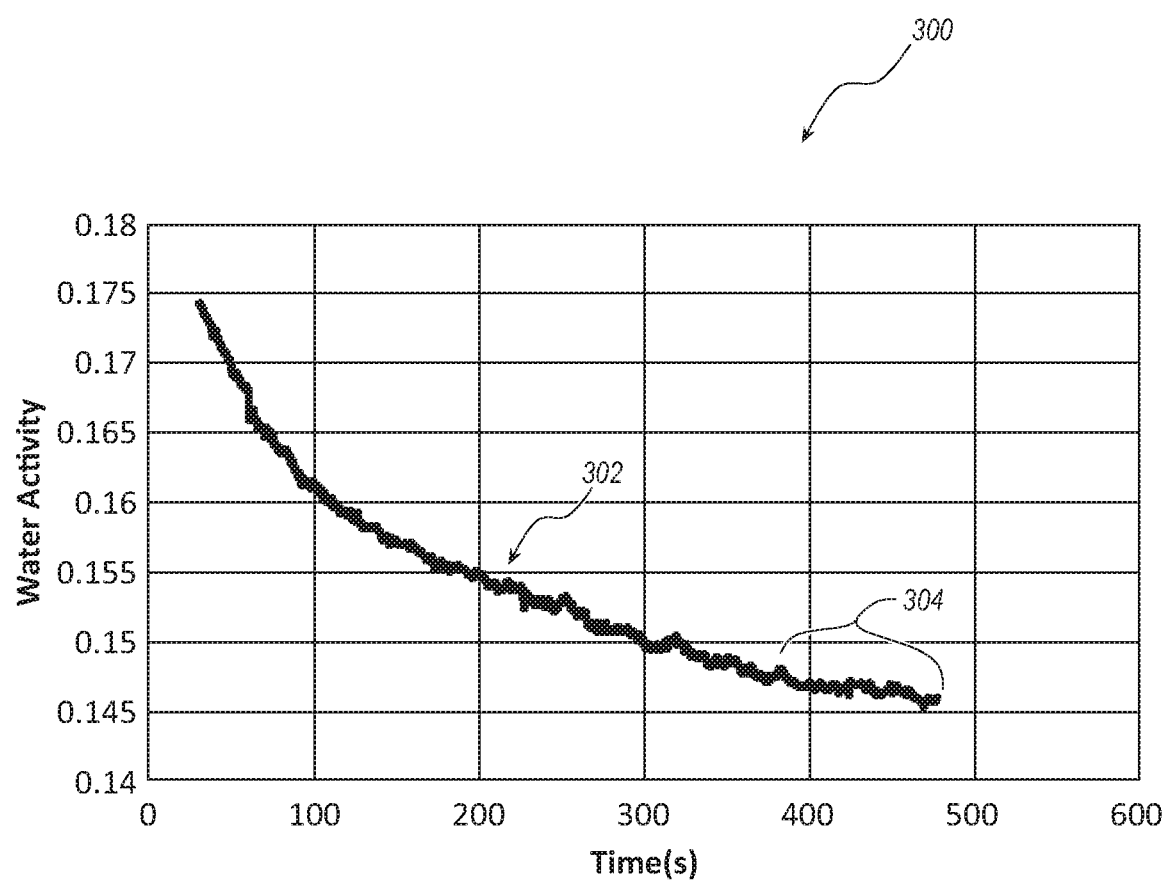
FIG. 3 is a plot of water activity values collected over time.

FIG. 3 shows a plot 300 of water activity measurements over time according to an example embodiment of the present disclosure. The data 302 associated with this plot 300 shows the water activity of a sample of potato chips equilibriating their relative humidity over time in a chamber of a typical water activity meter. Although potato chips are shown in this example, the systems and methods described herein have wide applicability, and have been tested and proven on products within a range of water activities below 0.20 to above 0.90. For example these products have included potato chips, peanut butter, infant formula, honey, beef jerky, raisins, dog kibble, ketchup, Parmesan cheese, and other, non-food products. These products represent a variety of product types that are well-suited for water activity measurement using instrumentation and related methods described herein. All of these products exhibit similar predictive accuracy using methods described herein.

As shown by the plotted data 302, the readings may be taken in high resolution in both time and water activity, with readings being taken about once per second. An initial portion of the data, such as the first about 30 seconds of data collected, can be discarded since it is commonly affected by transients and outliers that occur during the start of the readings. Accordingly, the values shown in the plot 300 do not include the first 30 seconds of water activity readings from the potato chips. After that initial period elapses, the water activity levels follow a substantially curved relationship in which the water activity decreases quickly at first, as shown in the time leading up to the first 100 seconds. Afterward, the water activity values gradually taper off in their rate of change until, as the sample reaches equilibrium, water activity value substantially levels off to a constant or significantly less-rapidly-decreasing number (as compared to the values between, for example, about 31 seconds and about 60 seconds), as indicated by the values 304 between about 390 seconds and about 480 seconds.

Generally speaking, the water activity of a sample material can reach equilibrium values (e.g., the end values 304) in a predictable amount of time, no matter what the water activity of the sample is at the start of the test. Accordingly, a plot 300 can be used to estimate a duration of time required for the a sample material to reach the equilibrium state in the water activity measurement device. For the potato chip example, it can be assumed that about 5 minutes and 30 seconds are required for a final water activity value to be measured using the equipment shown. The water activity decay curve for that material and for this water activity measurement device can be calculated from the values that are gathered in the test run shown in FIG. 3.

Figure 4:
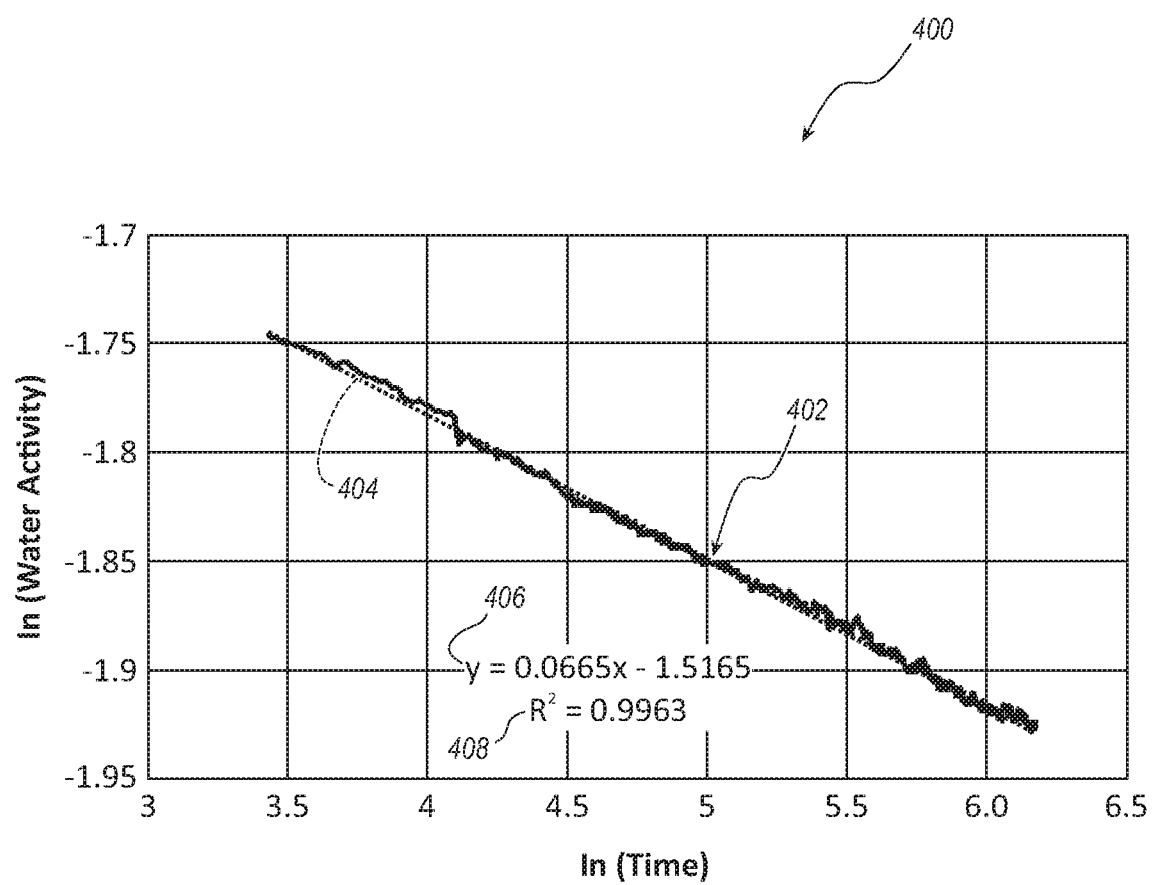
FIG. 4 shows log-transformed values of the plot of FIG. 3.

FIG. 4 shows a plot 400 of the natural logarithm of water activity data 302 as a function of the natural logarithm of the time at which each point of data in the plot 300 is measured (in seconds). Accordingly, the data 302 in FIG. 3 can be log-transformed to the curve of the plot 300 to obtain the series 402 in plot 400. This series 402, as shown in plot 400, follows a substantially straight line. A linear trendline 404 can be fit to the series 402 using data processing and curve-fitting techniques, such as least-squares regression. This linear trendline 404 can be represented by an equation 406 showing the relationship between the natural log of the water activity as is dependent on the natural log of the time elapsed. In this example data, the linear trendline 404 is a very close approximation of the series 402, as indicated by the R-squared value 408, which in this example is 0.9963. Other sample materials have similar variance for their regression trendlines.

Based on FIG. 4, the water activity change over time can be modeled by Equation 1:

$$\ln(a_w) = a \ln(t) + b \quad \text{(Equation 1)},$$

wherein a and b are constant values. The values of a and b can be determined by fitting a trendline 404 to the log-transformed data (or portion of that data). Beneficially, the trendline 404 does not have to be generated after the sample has reached equilibrium. Instead, the trendline can be obtained while the initial water activity measurements are being collected, such as during or immediately after the first minute or two of data collection. Because of the linear relationship between the log-transformed water activity and time, the water activity at a future time (e.g., at equilibrium) can be projected and extrapolated from the initial data collected. Thus, Equation 1 can be used to predict the water activity at a future time t, such as at the time of equilibrium of the sample in the water activity measurement device. In some cases, this prediction can be obtained well before the equilibrium time is reached, such as within about the first minute or 90 seconds of obtaining water activity measurements using the water activity measurement device.

The final water activity can be computed using the following equation, which is reconfigured from Equation 1:

$$a_{wf} = \exp[a \ln(t_f) + b] \quad \text{(Equation 2)}.$$

As explained above, the a and b coefficients can be obtained by generating a trendline from the log-transformed initial measurements. The value used for the anticipated equilibrium time ($t_f$) represents the duration of time that the water activity meter would normally require to complete obtaining a normal water activity measurement. For example, as indicated by the potato chip example data, the equilibrium time or final time $t_f$ may be about 5 minutes and 30 seconds from the start of the test. This final time $t_f$ can be obtained empirically from an original test sample or can be obtained from a database storing equilibrium times for various materials, as explained in further detail below.

Additionally, in some embodiments, only a rough idea of the time when the water activity reading will finish may be required to accurately estimate the final water activity of the sample material. As the overall measurement duration elapses, the water activity values change progressively more and more slowly due to the logarithmic relationship. In other words, the tapering effect of the end values 304 means that a precise time of equilibrium (e.g., at 432 seconds) may not be required to obtain a sufficiently accurate estimate of the equilibrium water activity measurement for the sample material. Instead, only a general or rough estimate of the equilibrium time may be needed. For example, the equilibrium time can be determined and recorded as a single value (e.g., about 5 minutes) with a range of acceptable deviation from that value (e.g., plus or minus 10 percent or 1 minute) within which the final water activity measurement negligibly varies from the single value. This characteristic of the measurement method can help to improve the robustness of the measurements using this technique by automatically accounting for minor variations in the initial relative humidity of the internal chamber 104, the ambient relative humidity, variations in the size or shape of the sample material, and other minor variables encountered in normal measurement operations. In some cases, an equilibrium time for a sample material can be replaced by an equilibrium range of times. For instance, if the water activity of a certain material tends to flatline around the 5 minute mark (e.g., at end values 304 in plot 300), an equilibrium range or range of acceptable values for the equilibrium time can be a range including 4 minutes and 45 seconds to 10 minutes or more.

In view of Equation 2, in some embodiments, set-up steps may need to be taken before a fast water activity estimate can be obtained. The set-up steps may include determining one or more equilibrium times $t_f$ (or a range or representative average/median of acceptable final times) using a conventional water activity measurement technique (e.g., waiting until a normal 5-30 minute water activity measurement is obtained). These times can then be stored in a database, such as a database of information held by a memory device 206, electronic storage device 210, or a network device 228.

Once this initial equilibrium time information is obtained and stored at a normal, relatively slow speed, it can be referenced in subsequent water activity measurements to greatly reduce the amount of time needed to obtain an estimated or predicted water activity of the same type of sample material using the methods described above in connection with Equations 1 and 2. In other words, once initial data for time $t_f$ is known, the final water activity of a sample can be extrapolated from initial data (e.g., at the start of data 302) by obtaining the trendline equation 406 for the initial data, determining the a and b coefficients described above, and using the final water activity equation with those coefficients and the predetermined final time $t_f$, even at measurement times well before the final time has actually been reached. In some configurations, a preexisting database of equilibrium water activity values for various products can be referenced by a user of the water activity measurement system in order to bypass and eliminate the need for the set-up measurement steps. For example, the database can be stored by network devices (e.g., 228) or another storage device (e.g., 210) of the system 200.

Accordingly, by collecting about 60 seconds of high resolution data, as shown in FIGS. 3 and 4, discarding the first about 30 seconds of that data (or however much is needed to discard and avoid initial transients), log-transforming the last 30 seconds of data (or however much remains after discarding the initial data with transients), then fitting a line to the transformed data (e.g., by least-squares regression) and using Equation 2 above with the stored value of $t_f$, the final water activity measurement of the sample material can be substantially instantaneously predicted at the end of the about 60 seconds of data collection rather than having to wait until the equilibrium time is actually reached.

The steps and methods outlined above may be effective for wide range of different types of products and can give high accuracy in the water activity measurements obtained. In a production environment, the water activity analysis times for a large number of different types of products (or ingredients thereof) in a factory system can be stored after a brief set up time wherein a small number (e.g., 1-5) of samples can be tested to obtain their equilibrium times in that particular factory system. In some cases, production environments can share sufficient similarities in their characteristics to enable a user to skip having to perform initial sample measurements by referencing previously-recorded equilibrium time data. This can be especially useful when a large number of different products or new products are made in a factory line. While a factory is in operation, a user can remove a sample material, can insert the sample material into the water activity measurement device, and can receive a water activity measurement within about one minute of the initial sample material removal, thereby allowing the user or facility operator to make relatively rapid adjustments to factors that will affect the final water activity at the production line. This also allows facility operators to save time while verifying batches of product after they are produced. Collected data can also be added back into a database to improve the reliability of stored data for future batches of the same or similar products and materials. For example, average, median, or similar data can be stored in a database for different materials in order to improve accuracy of the equilibrium time values used.

Figure 5:
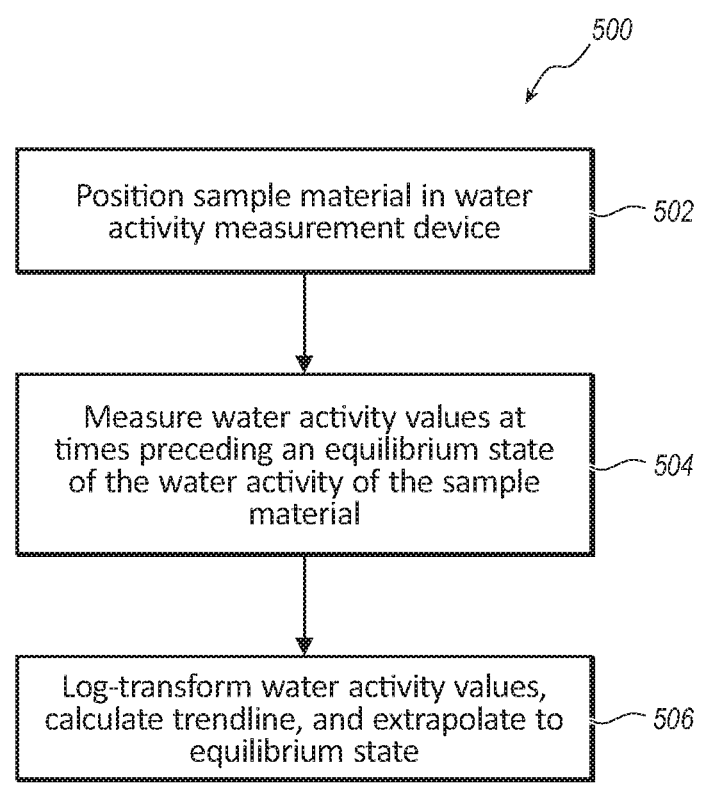
FIG. 5 is a block diagram of a method for determining water activity of a sample material.

FIG. 5 is a block diagram illustrating a particular example embodiment of a method 500 for determining water activity of a sample material. As explained herein, a system for implementing fast water activity measurements can comprise a water activity meter with the sample chamber capable of enclosing and sealing in a sample of the product and the water activity sensor capable of reading the water activity of the sample at a frequency of about one reading per second. The method 500 can therefore include positioning a sample material in the water activity measurement device, as indicated in block 502. Positioning the sample material in the water activity measurement device may comprise enclosing the simple material in a sealed chamber of the device, such as a sealed chamber that includes an airtight or vapor tight seal around a door or other movable side surface of the sealed chamber. This can also comprise obtaining a sample from an active production line or factory machine and quickly moving that sample into a testing device (i.e., while its water activity still substantially matches product on the production line).

The system can also include a firmware- or software-based application or computing device, which is in intimate communication with the water activity meter and its sensors, that receives information about the product being analyzed, what the typical analysis time is for that product (i.e., the final or equilibrium time), and what the safe and tolerable limits are for water activity in that product. Thus, the method 500 can include measuring a plurality of water activity values of the sample material at a respective plurality of points of time, with the plurality of points in time preceding an equilibrium state of the water activity of the sample material, as shown in block 504 and as shown illustratively in FIG. 3. The frequency of collection of the water activities measurements can, in some embodiments, be at least one measurement per second. In other words, water activity measurements can be collected at about one second intervals over the plurality of points of time, or the plurality of points in time can be about one second part. This frequency of data collection can ensure that variation and error in the water activity measurements can be accounted for when a trendline is generated because a sufficient number of data points is collected within the short timeframe of the testing period.

The collection of the water activity values can conclude at about 60 seconds, about 90 seconds, or about 120 seconds from the starting time of the collection of those values. As disclosed herein, the conclusion times can vary depending on the sample material being tested, the desired accuracy of the measurement of the final water activity, the accuracy of the instruments used to test the water activity, and similar factors, or combinations thereof. In some cases, the collection time can be extended beyond an initial test conclusion time (e.g., past 60 seconds, 90 seconds, etc.) based upon how the projected results at that initial conclusion time fit within an accuracy range or acceptable reading threshold range. This is discussed in greater detail in connection with FIG. 6 below.

Finally, the system can include software or firmware configured to log-transform the collected water activity and time data from the sensor and to perform the calculations described above. Thus, the method 500 can include log-transforming the plurality of water activity values over time, calculating a trendline of the plurality of water activity values over time, and extrapolating the trendline to determine an extrapolated water activity value of the sample material at the equilibrium state, as shown in block 506.

As explained above, the extrapolated water activity value of the sample material at the equilibrium state can be determined before the sample material reaches the equilibrium state inside the water activity measurement device. Furthermore, in response to the occurrence of transients in the water activity values, and initial portion of the plurality of points of time may be discarded or ignored when calculating the trendline. This can allow the trendline to be based on more reliable and consistent water activity data.

In some cases, the method 500 can further include detecting a characteristic of the sample material, such as detecting the type or composition of the sample material before determining the extrapolated water activity value at the equilibrium state. In order to perform this function, the water activity measurement device or a related device of the system can detect a physical or chemical characteristic of the simple material. For example, the system can comprise an image sensor, a near infrared (NIR) or Raman spectroscopy sensor, a dielectric sensor, or an optical particle size sensor. These sensors can be part of the sensors 230 described above. With an image sensor, for example, red-green-blue (RGB) images can be used to identify products when there are significant texture, color, or shape attributes of that type of product that allow it to be discriminated from other product types. A spectroscopy sensor can take advantage of the fact that specific materials will exhibit unique spectral responses based on their composition and the physical state of the product. Whether near infrared or Raman spectroscopy sensors are used, the sensor system can illuminate the sample and measure the reflected or scattered light. Raman spectroscopy can be especially useful in situations where product types are very similar to each other by detecting trace amounts of specific materials. Dielectric spectroscopy instruments can be used to measure the frequency response of the product when it is unique. For example, different polar molecules will exhibit relaxation effects at specific frequencies that can be used to infer product type. With an optical particle size sensor, techniques such as laser scattering can be used to measure the particle size in the sample. This information can be used to identify products based on the particle sizes and their texture.

The system can comprise a connection to a database that includes preferable limits for water activity of the product being tested. The limits can be user-defined or based on a history of testing. Based on those limits, and the known uncertainties in the predicted water activity and those limits, the system can determine and display that the predicted water activity reading for the equilibrium state is within a desired range, outside the desired range, or, potentially, too close to call without obtaining additional precision in the measurement. In the latter case, for example, the water activity value may be at the edge of the acceptable range of water activity values for that sample material, and therefore may need additional data collection in order to conclude whether the water activity is within the acceptable range or not.

In order to obtain additional precision and a more accurate estimate, the system (e.g., 200) may be enabled to extend the measurement period (e.g., extend the measurement period beyond 60 seconds, 90 seconds, 120 seconds, or whatever duration is used to obtain a first estimate of the equilibrium water activity value). During the extension of time, measurements of the water activity can continue to be collected over a plurality of points in time, such as one water activity value measurement per second for an additional 15, 30, or 45 seconds. In some embodiments, the extension period of time can be less than or equal to the duration of time from which measurements of the water activity are not discarded due to transients. For example, if the first 30 seconds of readings are discarded, and the next 30 seconds of readings are used to obtain the first equilibrium water activity value estimate, then the system can extend up to an additional 30 seconds to obtain about 30 more water activity data points. By increasing the amount of data collected, and by collecting data even closer to the equilibrium time, the accuracy and precision of the equilibrium water activity estimate increases. Therefore, when a second estimate is obtained, such as by calculating a second trendline that takes into account the first collected data set and the second collected data set, the system can better extrapolate that trendline to determine whether the water activity of the sample material falls within or without the range of acceptable water activity values.

At times, the second equilibrium water activity estimate can still be too close to the edge between acceptable and unacceptable values. Accordingly, the system can be configured to still further continue obtaining water activity measurements over an additional extended time period (e.g., 15, 30, or 45 seconds longer) and obtain a third estimate. This process can continue indefinitely (e.g., four, five, six, or more estimates) until (a) the projected equilibrium water activity value is known with enough precision to conclude extending the test or (b) the sample material finally reaches actual equilibrium in the testing device and a non-projected and non-estimated water activity value measurement is obtained, such as by using the chilled mirror dew point sensor.

When a projected or estimated water activity value is determined, an indication of the status of the projected water activity value can be produced. For example, the water activity meter 100 can comprise an indicator (e.g., 234) such as a visual indicator (e.g., a light or display screen) or an audio indicator (e.g., a speaker or vibrator) configured to output a signal when a projected water activity value has been calculated in accordance with the methods described above. The output of the indicator can comprise two or more different signals. For instance, a visual indicator can output two or more different colors, words, shapes, symbols, or similar indicators and an audio indicator can output two or more different sounds, vibration patterns, or similar indicators, wherein each indicator is used to represent a different status or result of the water activity measurement.

In one embodiment, the output can consist of two types of signals, wherein one type of signal is output to indicate an acceptable water activity value and the other type of signal is output to represent an unacceptable water activity value. For example, for a sample material, the measured water activity of the sample may be desired to be within a range of acceptable values, and the indicator can therefore indicate, using the two signals, whether the water activity of the tested sample is within the acceptable range or not. In some configurations, a visual indicator can emit green light (or another color or indicator pattern) to represent an acceptable or in-spec water activity estimate and can emit a red light (or turn off, blink in a different pattern, or provide any other type of alternative indicator) to represent an unacceptable or out-of-spec water activity estimate. In this case, the water activity measurement system does not indicate that a water activity value is very close to the border or threshold between acceptable values and unacceptable values.

In another embodiment, the output can comprise three or four signals, wherein two of the signals indicate acceptable and unacceptable measurements, and the third signal (and fourth signal, if applicable) indicates a measurement that lacks sufficient precision to determine whether the measurement is acceptable or unacceptable. In other words, the third signal (and potentially fourth signal) indicates that the measurement is near the threshold between in-spec and out-of-spec water activity values and that additional measurements are needed to obtain sufficient precision to determine the side of the threshold on which the sample lies. In embodiments with three signals, the third signal can represent a single threshold (i.e., all values above the threshold are acceptable, and all values below are unacceptable, or vice versa). Embodiments with four signals can be used when a range or band of acceptable or unacceptable water activity measurements is defined. The third signal can indicate that the measurement is near the lower end of that range or band, and the fourth signal can indicate that the measurement is near the upper end thereof. In some configurations, the indicator produced for the third and fourth signals can be identical, such as by causing the indicator to output blue light in either case. In some cases, a different indicator can be produced for the third and fourth signals (e.g., blue for the third indicator and white for the fourth signal). In some embodiments, a different indicator can be output for the third or fourth signal as compared to first and second signals (e.g., blue light for the third and/or fourth signals and green/red for the first two, as explained above). In yet another embodiment, the third signal can be used to indicate a measurement at both the top end and the bottom end of a range or band of acceptable values. As with the first and second signals, the third and fourth signals can vary from each other, and the first and second signals, by providing a different visual or audible indicator, such as a different color, display pattern, sound, vibration, or similar indication variation.

Figure 6:
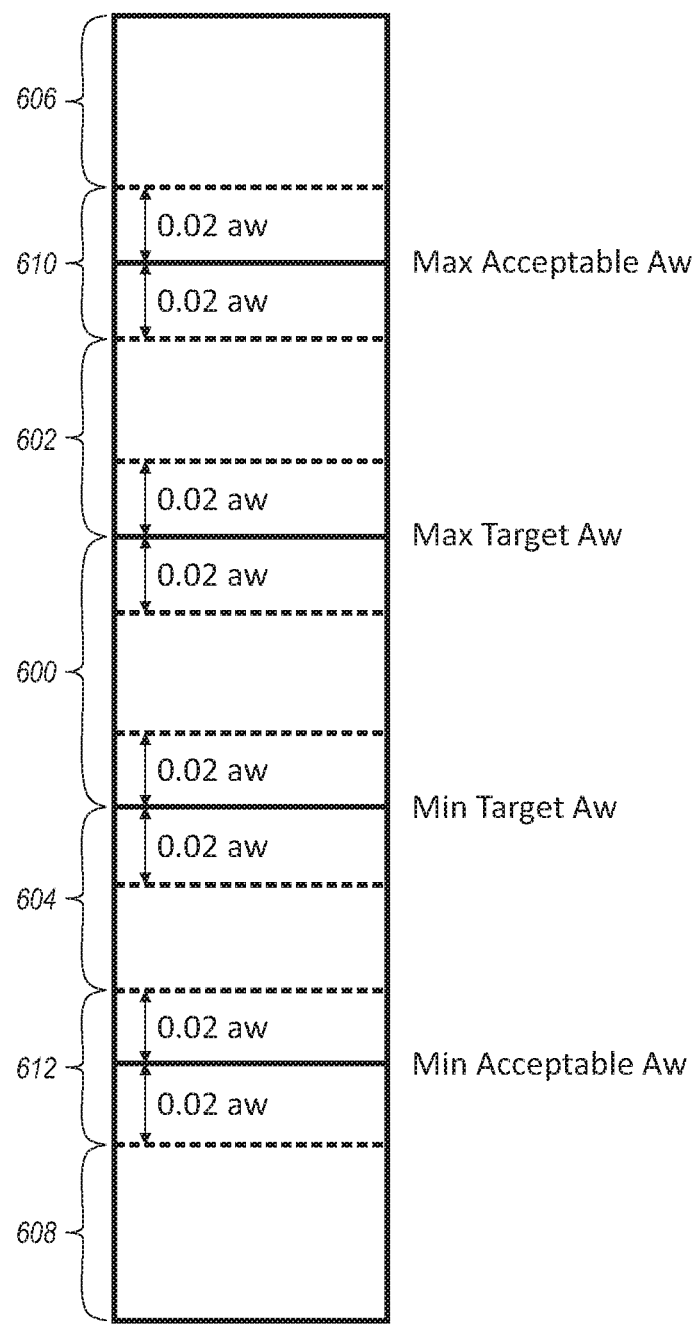
FIG. 6 is a diagram illustrating how multiple ranges of acceptable water activity values can be used to indicate results of a water activity test of a sample material.

Furthermore, in some embodiments, multiple ranges of values and statuses can be indicated. FIG. 6 is a diagram illustrating how multiple ranges of acceptable water activity values can be used to conduct a water activity test of a sample material. A first range 600 can represent an optimal, preferred, or target range of water activity values. An indicator (e.g., a green light) can be produced if the projected or estimated water activity measurement lies between the upper and lower bounds of the first range 600 (i.e., between the maximum target water activity and the minimum target water activity).

A second range 602 can represent a range of less-optimal, less-preferred, or fringe-acceptable water activity values. In some embodiments, the range can be between a maximum target water activity and a maximum acceptable water activity, as shown in FIG. 6. A different indicator (e.g., a yellow light) can be produced if the projected or estimated water activity measurement lies within that range 602. The second range 602 can be higher than the upper boundary of the first range 600. A third range 604 can be similar to the second range 602 but is lower than the lower boundary of the first range 600 and corresponds to the span of values between the minimum target water activity and the minimum acceptable water activity.

Outer ranges 606, 608 can represent unacceptable ranges of water activity values. Another indicator (e.g., a red light) can be emitted when the estimated water activity lies within those ranges 606, 608. In some embodiments, an error band (e.g., 610, 612) can be positioned at the transition between each range 600, 602, 604, 606, 608 or between specified ranges. As shown in FIG. 6, these bands 610, 612 can correspond to percentage variations in the target or acceptable water activity values for a sample material. In this example, a plus or minus 2 percent variation is indicated, but other percentages can be used, depending on the user needs or the material being tested. When an estimated water activity value measurement lies within an error band, a different signal (e.g., a blue light of the third or fourth signals, as discussed above) can be produced. The error bands can have a width that is based on a percentage or proportion of the size of the other ranges (e.g., 600, 602, 604) and can be dependent upon the type of material being tested, the amount of material, or other variable testing conditions. As explained above, when a measurement lies within an error band 610, 612, the system can be configured to extend the testing period of time and collect more water activity measurements until the water activity estimate lies outside the error bands (e.g., in ranges 600, 602, 604, 606, or 608 external to the error bands) or until the actual equilibrium water activity value is measured.

Embodiments of the present disclosure can be used by quality assurance, production, and operations groups in food, pharmaceutical, and chemical production operations. Fast water activity measurement can also be implemented as part of a subset of an overall food processing management system which can be used by nearly all operating groups within food, pharmaceutical, and chemical producing companies.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:

1. A method of determining water activity of a sample material, the method comprising:
   positioning a sample material in a water activity measurement device;
   measuring a plurality of water activity values of the sample material at a respective plurality of points of time, the plurality of points in time preceding an equilibrium state of the water activity of the sample material;
   determining the values of a and b for $\ln(a_{wi}) = a \ln(t_i) + b$ which best fit a group of the plurality of water activity values up to a time preceding the equilibrium state, wherein $a_{wi}$ is a water activity value of the plurality of water activity values corresponding to a respective time $t_i$ of the respective plurality of points in time; and
   calculating an extrapolated water activity value from $a_{wf} = \exp(a \ln(t_f) + b)$, wherein $a_{wf}$ is the extrapolated water activity value at the equilibrium state, and $t_f$ is a material-specific equilibrium time for the sample material determined prior to measuring the plurality of water activity values of the sample material at the respective plurality of points of time.

2. The method of claim 1, wherein the extrapolated water activity value of the sample material at the equilibrium state is determined before the sample material reaches the equilibrium state in the water activity measurement device.

3. The method of claim 1, further comprising discarding a second group of the plurality of water activity values corresponding to an initial portion of the plurality of points in time before calculating the extrapolated water activity value.

4. The method of claim 1, wherein positioning the sample material comprises enclosing the sample material in a sealed chamber of the water activity measurement device.

5. The method of claim 1, wherein the plurality of water activity values are all determined within a measurement time duration of less than a time duration required for the sample material to reach the equilibrium state.

6. The method of claim 1, wherein at least 30 water activity values are measured in the plurality of points in time.

7. The method of claim 1, further comprising:
   detecting a physical or chemical characteristic of the sample material; and
   determining the material-specific equilibrium time $t_f$ based on the physical or chemical characteristics of the sample material before calculating the extrapolated water activity value $a_{wf}$.

8. The method of claim 1, further comprising: prior to calculating the extrapolated water activity value, measuring a water activity of the sample material at the equilibrium state; and calculating the material-specific equilibrium time tf for the sample material to reach equilibrium.

9. The method of claim 1, further comprising obtaining the material-specific equilibrium time $t_f$ from a database of material-specific equilibrium times.

10. A water activity measurement apparatus, comprising:
    a measurement chamber;
    a water activity sensor in the measurement chamber;
    a processor;
    memory in electronic communication with the processor;
    instructions stored in the memory, the instructions being executable by the processor to:
      determine, by the water activity sensor, a plurality of water activity values of a sample material in the measurement chamber over a respective plurality of points in time, the plurality of points in time preceding an equilibrium state of the water activity of the sample material;
      determine the values of a and b for $\ln(a_{wi}) = a \ln(t_i) + b$ which best fit a group of the plurality of water activity values up to a time preceding the equilibrium state, wherein $a_{wi}$ is a water activity value of the plurality of water activity values corresponding to a respective time $t_i$ of the respective plurality of points in time; and calculate an extrapolated water activity value from $$a_{wf}=\exp(a\,\ln(t_f)+b),$$

wherein $a_{wf}$ is the extrapolated water activity value at the equilibrium state, and $t_f$ is a material-specific equilibrium time for the sample material determined prior to determining, by the water activity sensor, the plurality of water activity values of the sample material in the measurement chamber over the respective plurality of points in time.

11. The apparatus of claim 10, wherein the instructions are configured to determine the extrapolated water activity value of the sample material at the equilibrium state before the sample material reaches the equilibrium state in the water activity measurement apparatus.

12. The apparatus of claim 10, wherein the instructions further comprise discarding a second group of the plurality of water activity values corresponding to an initial portion of the plurality of points of time before calculating the extrapolated water activity value.

13. The apparatus of claim 10, wherein the plurality of water activity values are configured to all be determined within a measurement time duration of less than a time duration required for the sample material to reach the equilibrium state.

14. The apparatus of claim 10, wherein the instructions are further executable to:

detect a physical or chemical characteristic of the sample material; and determine the material-specific equilibrium time $t_f$ based on the physical or chemical characteristics of the sample material before calculating the extrapolated water activity value $a_{wf}$.

15. The apparatus of claim 10, wherein the instructions are further executable by the processor to: prior to calculating the extrapolated water activity value, measure a water activity of the sample material at the equilibrium state; and calculate the material-specific equilibrium time tf for the sample material to reach the equilibrium state.

16. The apparatus of claim 10, wherein the instructions are further executable by the processor to obtain the material-specific equilibrium time $t_f$ from a database of material-specific equilibrium times.

17. A non-transitory computer-readable medium storing computer-executable code for measuring water activity of a sample material, the code executable by a processor to:

determine, by a water activity sensor, a plurality of water activity values of a sample material in a measurement chamber over a respective plurality of points in time, the plurality of points in time preceding an equilibrium state of the water activity of the sample material;

determine the values of a and b for $$\ln(a_{wi})=a\,\ln(t_i)+b$$

which best fit a group of the plurality of water activity values up to a time preceding the equilibrium state, wherein $a_{wi}$ is a water activity value of the plurality of water activity values corresponding to a respective time $t_i$ of the respective plurality of points in time; and calculate an extrapolated water activity value from $$a_{wf}=\exp(a\,\ln(t_f)+b),$$

wherein $a_{wf}$ is the extrapolated water activity value at the equilibrium state and $t_f$ is a material-specific equilibrium time for the sample material determined prior to determining, by the water activity sensor, the plurality of water activity values of the sample material in the measurement chamber over the respective plurality of points in time.

18. The non-transitory computer-readable medium of claim 17, wherein the code is configured to determine the extrapolated water activity value of the sample material at the equilibrium state before the sample material reaches the equilibrium state in the measurement chamber.

19. The non-transitory computer-readable medium of claim 17, wherein the code further comprises discarding a second group of the plurality of water activity values corresponding to an initial portion of the plurality of points of time before calculating the extrapolated water activity value.

20. The non-transitory computer-readable medium of claim 17, wherein the plurality of water activity values are configured to all be determined within a measurement time duration of less than a time duration required for the sample material to reach the equilibrium state.

21. The non-transitory computer-readable medium of claim 17, wherein the code is further executable to:

detect a physical or chemical characteristic of the sample material; and determine the material-specific equilibrium time $t_f$ based on the physical or chemical characteristics of the sample material before calculating the extrapolated water activity value $a_{wf}$.

22. The non-transitory computer-readable medium of claim 17, wherein the code is further executable by the processor to: prior to calculating the extrapolated water activity value, measure a water activity of the sample material at the equilibrium state; and calculate the material-specific equilibrium time tf for the sample material to reach the equilibrium state.

23. The non-transitory computer-readable medium of claim 17, wherein the code is further executable by the processor to obtain the material-specific equilibrium time $t_f$ from a database of material-specific equilibrium times.

* * * * *